(12) United States Patent
Bonthuys (10) Patent No.: US 7,083,570 B2
(45) Date of Patent: Aug. 1, 2006

(54) DEVICE FOR THE TREATMENT OF ERECTILE DYSFUNCTION

(75) Inventor: Barend Willem Bonthuys, Moreleta Park (ZA)

(73) Assignee: Maria Emmerentia Bonthuys, Pretoria (ZA)

( * ) Notice: Subject to any disclaimer, the term of this patent is extended or adjusted under 35 U.S.C. 154(b) by 66 days.

(21) Appl. No.: 10/913,272

(22) Filed: Aug. 6, 2004

(65) Prior Publication Data
US 2005/0033113 A1 Feb. 10, 2005

(30) Foreign Application Priority Data
Aug. 7, 2003 (ZA) .................... 2003/6116

(51) Int. Cl.
*A61F 5/00* (2006.01)
(52) U.S. Cl. ....................................... 600/41
(58) Field of Classification Search ............. 600/38–41
See application file for complete search history.

(56) References Cited

U.S. PATENT DOCUMENTS

| | | | |
|---|---|---|---|
| 4,602,625 A | 7/1986 | Yachia et al. | |
| 4,671,262 A * | 6/1987 | West | 600/39 |
| 4,753,227 A * | 6/1988 | Yanuck, Jr. | 600/41 |
| 4,892,517 A | 1/1990 | Yuan et al. | |
| 5,095,895 A | 3/1992 | Walsh | |
| 5,213,563 A | 5/1993 | Cox | |
| 5,338,288 A | 8/1994 | Finkle | |
| 5,344,389 A | 9/1994 | Walsdorf et al. | |
| 5,421,808 A | 6/1995 | Osbon et al. | |
| 5,462,514 A | 10/1995 | Harris | |
| 5,622,186 A | 4/1997 | Schwartz | |
| 5,624,378 A | 4/1997 | Baldecchi | |
| 5,782,621 A | 7/1998 | Harris | |
| 6,036,635 A | 3/2000 | Altshuler | |
| 6,248,059 B1 | 6/2001 | Gamper et al. | |
| 6,302,305 B1 | 10/2001 | Bonningue | |
| 6,390,095 B1 * | 5/2002 | Magnusson | 128/842 |
| 6,458,073 B1 | 10/2002 | Bonthuys | |
| 2004/0171911 A1 * | 9/2004 | Zurita | 600/38 |

FOREIGN PATENT DOCUMENTS

CH 347300 8/1960

OTHER PUBLICATIONS

English Translation of CH 347300 Dated Aug. 15, 1960.

* cited by examiner

*Primary Examiner*—John P. Lacyk
(74) *Attorney, Agent, or Firm*—Ladas and Parry LLP (57) ABSTRACT

A device 10 for use in the treatment of erectile dysfunction or for penile exercise includes an elongate vessel 12 defining a vacuum chamber 16. The vessel 12 has at one end thereof a mouth opening 18 leading into the vacuum chamber 12. The vacuum chamber 16 is shaped and dimensioned to receive a penis. The device 10 further includes a valve arrangement 14 positioned at or towards the other end of the vessel 12. The valve arrangement 14 incorporates both a non-return valve 34 to permit air to be extracted from and a vacuum to be drawn in the vacuum chamber 16, and a selectively operable vacuum relief valve.

32 Claims, 6 Drawing Sheets

DEVICE FOR THE TREATMENT OF ERECTILE DYSFUNCTION

THIS INVENTION relates to a device and to apparatus for use in the treatment of erectile dysfunction or for penile exercise in the human male.

A problem that occasionally occurs in human males is the inability to attain an erection of the penis.

It is thus an object of the invention to provide a device which may be used particularly but not necessarily exclusively in the treatment of erectile dysfunction and for penile exercise, and which is not unwieldy or cumbersome when used in intimate situations.

According to one aspect of the invention there is provided a device for use in the treatment of erectile dysfunction or for penile exercise which includes:

an elongate vessel defining a vacuum chamber and having at one end of the vessel a mouth opening leading into the vacuum chamber, the vacuum chamber being shaped and dimensioned to receive a penis; and a valve arrangement positioned at or towards the other end of the vessel, the valve arrangement incorporating both a non-return valve to permit air to be extracted from and a vacuum to be drawn in the vacuum chamber, and a selectively operable vacuum relief valve.

The valve arrangement may include a hole extending through the vessel and a seal element displaceable between a closed position, towards which it is biased, and in which it permits the flow of air from inside the vessel through the hole to outside the vessel and inhibits flow of air from outside the vessel to inside the vessel, and an open position which permits the flow of air through the hole both into and out of the vessel.

The seal element may be in the form of a resilient deformable flap which functions in its closed position as a non-return valve to permit air to be drawn from the vacuum chamber and inhibit the flow of air into the vacuum chamber.

The seal element may be mounted on a support which is mounted on the vessel and at least part of which is displaceable between a rest position towards which it is biased, in which the seal element functions as a non-return valve and a displaced position, in which the seal element is displaced to its open position in which it is clear of the hole to permit air flow therethrough.

The seal element and the support may be formed as a unitary moulding of a synthetic plastics material.

The device may include seal means positioned in the vicinity of the mouth opening and configured to engage with an outer surface of a human penis inserted into the vacuum chamber.

The seal means may include a sealing constriction ring which is readily dismountably mounted on the vessel in the vicinity of the mouth opening, the constriction ring including a generally ring-shaped body having a circumferentially extending engagement formation for releasable sealing engagement with the vessel in the vicinity of the mouth opening and a constriction ring opening configured sealingly to abut against the outer surface of a human penis.

The body of the constriction ring may be formed as a unitary moulding of an elastomeric material. The elastomeric material may be silicon rubber having a hardness of about 50 A Shore.

The size of the constriction ring opening will depend on the intended application. Hence, when intended for use in the treatment of erectile dysfunction, the opening will be sufficiently small to inhibit blood flow from the penis once an erection is attained in order to maintain the erection. In contrast, when the device is intended to be used for penile exercise, the opening will be sufficiently small to seal against the surface of the penis and sufficiently large to permit blood to drain from the erect penis.

The constriction ring opening may have a diameter of between 13 and 30 mm.

The device may include a plurality of interchangeable sealing constriction rings, each having a constriction ring opening of a different size.

The device may include supplementary pumping means, at least part of which is mounted for reciprocation relative to the vessel, for pumping air out of the vacuum chamber.

The supplementary pumping means may include a pumping member, mounted on and slidingly displaceable relative to the vessel, the vessel and pumping member being shaped and configured so that the vessel and the pumping member together form a vacuum chamber and so that sliding displacement of the pumping member and the vessel relative to one another changes the volume of the suction chamber;

at least one pumping passage extending between the vacuum chamber and the suction chamber;

at least one exhaust passage leading from the suction chamber;

first one way valve means which permits fluid flow from the vacuum chamber to the suction chamber via the, or each, pumping passage; and second one way valve means which permits fluid to be discharged from the suction chamber via the or each exhaust passage to atmosphere.

The vessel may have an outer surface which is substantially cylindrical for at least part of its length, the pumping member extending around the cylindrical portion of the outer surface of the vessel and being longitudinally slidingly displaceable relative thereto.

The or each pumping passage may be positioned and the pumping member may be arranged so that displacement of the pumping member towards the mouth of the vessel increases the volume of the suction member and causes air to flow from the vacuum chamber through the or each pumping passage into the suction chamber and displacement of the pumping member away from the mouth of the vessel decreases the volume of the suction chamber causing air to be discharged from the suction chamber through the or each exhaust passage to atmosphere.

According to another aspect of the invention there is provided apparatus for use in the treatment or erectile dysfunction or for penile exercise which includes an elongate vessel defining a vacuum chamber and having at one end of the vessel a mouth opening leading into the vacuum chamber, the vacuum chamber being shaped and dimensioned to accommodate an erect human penis;

a non-return valve mounted on the vessel to permit air to be extracted from and a vacuum to be drawn in the vacuum chamber; and a vacuum pump which is readily disconnectably connectable in flow communication with the vacuum chamber.

The apparatus may include a seal arrangement to provide a seal between the vessel and the vacuum pump when the pump is being held manually in position to connect the pump and the vacuum chamber in flow communication thereby to permit a vacuum to be drawn in the vacuum chamber.

Hence, in use, when a vacuum has been drawn in the vacuum chamber, the pump can be readily removed and does not remain connected to the vessel without affecting the vacuum which has been drawn in the vacuum chamber.

The other end of the vessel, i.e. the end remote from the mouth, may be domed and the non-return valve may be provided at or towards the other end of the vessel.

The seal arrangement may include a body which defines a pump engaging seat and a vessel engaging seat for engaging sealingly against the pump and the vessel respectively.

The vessel engaging seat may be of a resiliently deformable material shaped and dimensioned to seat sealingly against an outer surface of the vessel around the non-return valve when held in abutment therewith.

The vessel engaging seat may be annular and have a contact surface which is part spherical in order to contact the domed end of the vessel around the valve.

The valve arrangement may include a hole extending through the vessel and a seal element displaceable between a closed position, towards which it is biased, in which it permits the flow of air from inside the vessel through the hole to outside the vessel and inhibits flow of air from outside the vessel to inside the vessel, and an open position in which it permits the flow of air through the hole both into and out of the vessel.

The seal element may be in the form of a resiliently deformable flap which functions in its closed position as a non-return valve to permit air to be drawn from the vacuum chamber and inhibit the flow of air into the vacuum chamber.

The seal element may be mounted on a support which is mounted on the vessel and at least part of which is displaceable between a rest position, towards which it is biased, and in which the seal element functions as a non-return valve and a displaced position, in which the seal element is displaced to its open position in which it is clear of the hole to permit air flow therethrough.

The seal element and the support may be formed as a unitary moulding of a synthetic elastomeric material.

The apparatus may include seal means positioned in the vicinity of the mouth opening and configured to engage with an outer surface of a human penis inserted into the vacuum chamber.

The seal means may include a sealing constriction ring which is readily dismountably mounted on the vessel in the vicinity of the mouth opening, the constriction ring including a generally ring shaped body having a circumferentially extending engagement formation for releasable or sealing engagement with the vessel in the vicinity of the mouth opening and a constriction ring opening configured sealingly to abut against the outer surface of a human penis.

The body of the constriction ring may be formed as a unitary moulding of an elastomeric material.

The elastomeric material may be silicon rubber having a hardness of about 50 A Shore.

The constriction ring opening may have a diameter of between 13 and 30 mm.

The apparatus may include a plurality of interchangeable sealing constriction rings, each having a constriction ring opening of a different size.

The vacuum pump may be manually or electrically operable.

The apparatus may include supplementary pumping means, at least part of which is mounted for reciprocation relative to the vessel, for pumping air out of the vacuum chamber.

The supplementary pumping means may include a pumping member, mounted on and slidingly displaceable relative to the vessel, the vessel and pumping member being shaped and configured so that the vessel and the pumping member together form a suction chamber and so that sliding displacement of the pumping member and the vessel relative to one another changes the volume of the suction chamber;

at least one pumping passage extending between the vacuum chamber and the suction chamber;

at least one exhaust passage leading from the suction chamber;

first one way valve means which permits fluid flow from the vacuum chamber to the suction chamber via the, or each, pumping passage; and second one way valve means which permits fluid to be discharged from the suction chamber via the or each exhaust passage to atmosphere.

The vessel may have an outer surface which is substantially cylindrical for at least part of its length, the pumping member extending around the cylindrical portion of the outer surface of the vessel and being longitudinally slidingly displaceable relative thereto.

The or each pumping passage may be positioned and the pumping member may arranged so that displacement of the pumping member towards the mouth of the vessel increases the volume of the suction chamber and causes air to flow from the vacuum chamber through the or each pumping passage into the suction chamber and displacement of the pumping member away from the mouth of the vessel decreases the volume of the suction chamber and causes air to be discharged from the suction chamber through the exhaust passage to atmosphere.

The invention will now be described, by way of example, with reference to the accompanying diagrammatic drawings.

Figure 1:
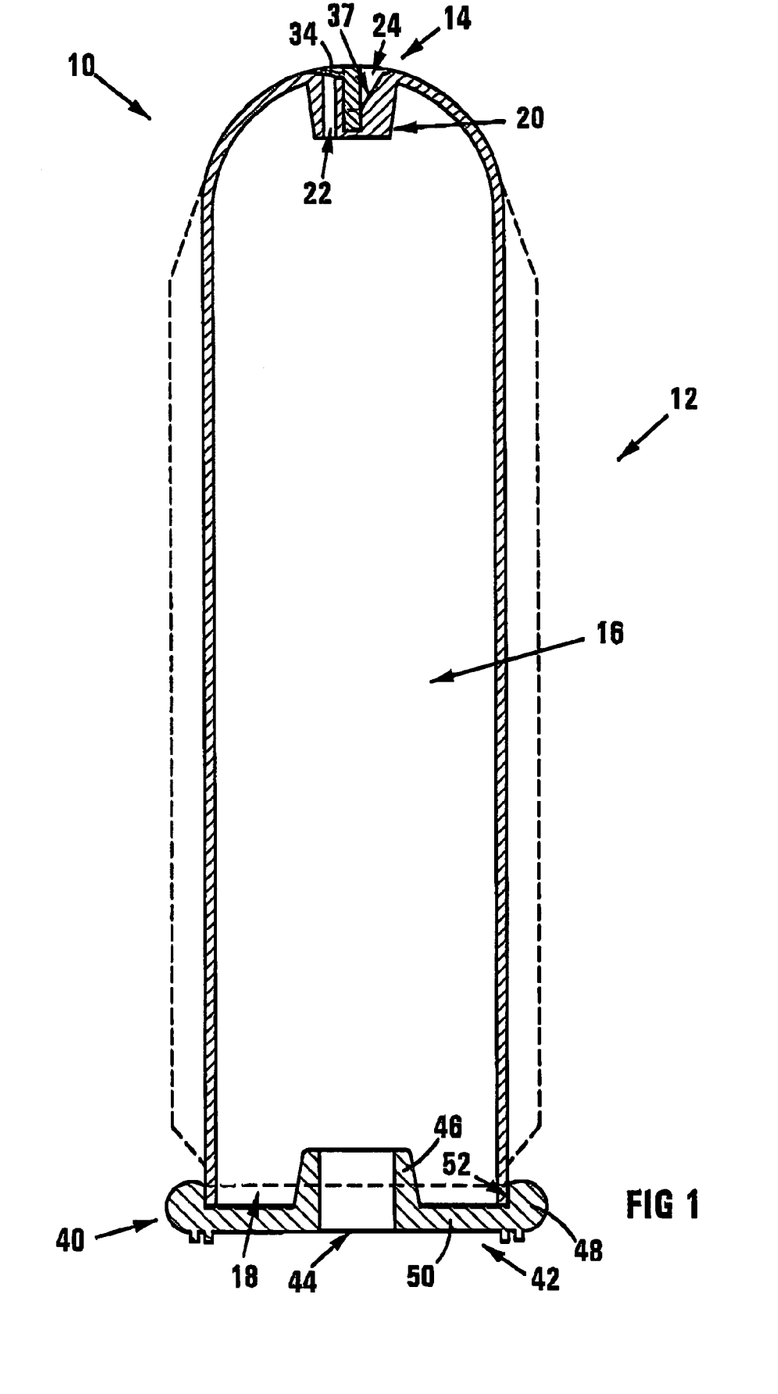
FIG. 1 shows a sectional side view of a device for use in the treatment of erectile dysfunction in accordance with the invention.
Figure 2:
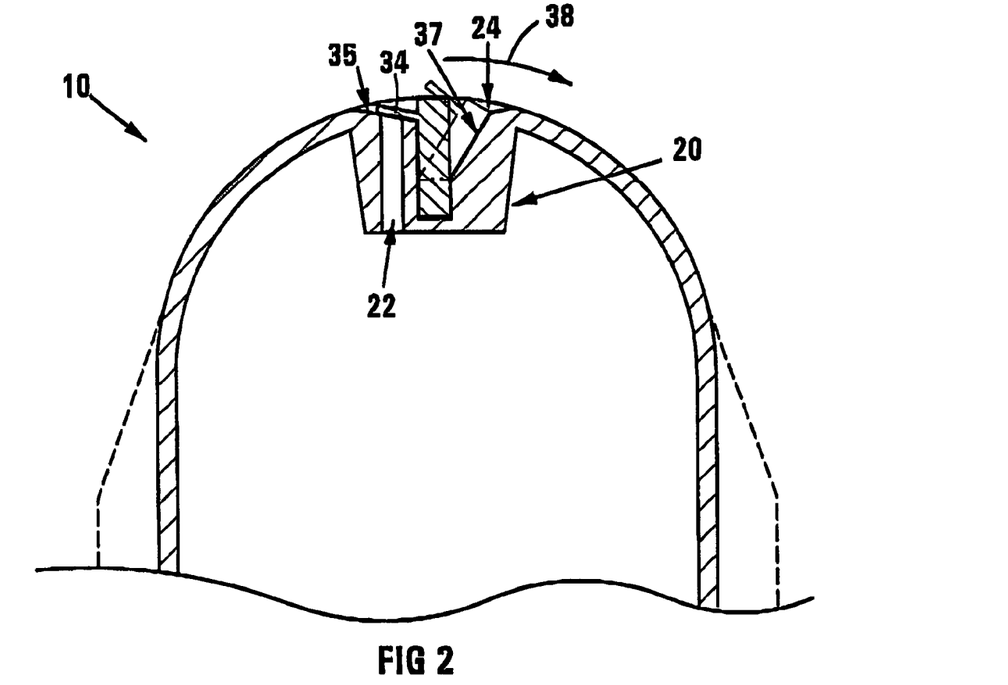
FIG. 2 shows, on an enlarged scale, a sectional view of an end portion of the device of FIG. 1.
Figure 3:
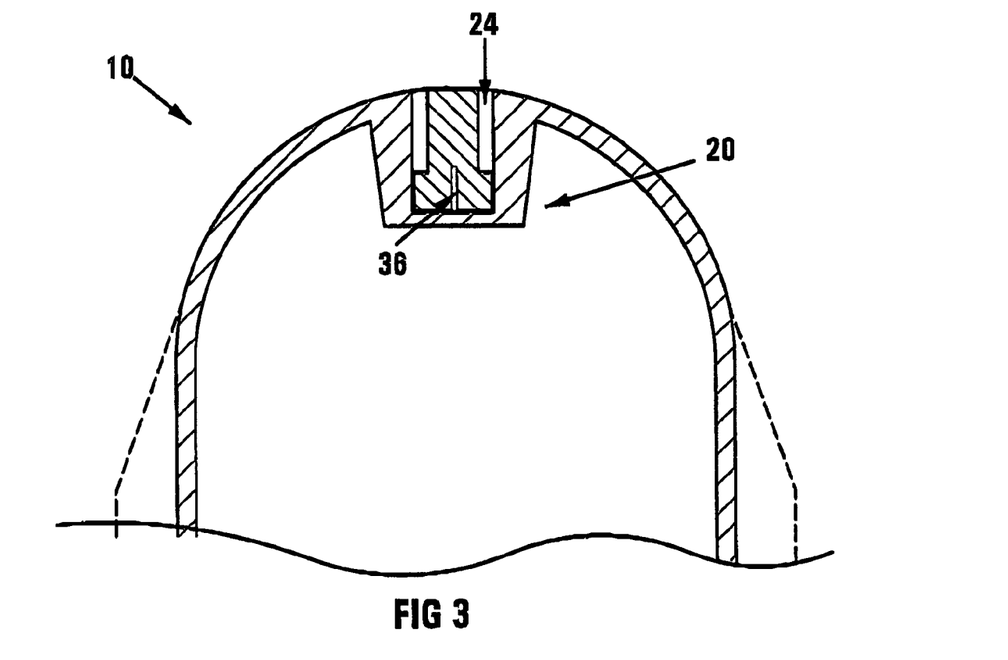
FIG. 3 shows a sectional view, similar to FIG. 2, taken at 90° to the section of FIG. 2.

In FIGS. 1 to 3 of the drawings, reference numeral 10 refers generally to a device for use in the treatment of erectile dysfuntion in accordance with the invention.

The device 10 includes a vessel 12 and a valve arrangement, generally indicated by reference numeral 14.

The vessel 12 is elongate and generally cigar-shaped and defines a vacuum chamber 16. As an alternative, a portion of the vessel may be of increased diameter as shown by the broken lines in FIG. 1.

The vessel 12 has, at one end thereof, a mouth opening 18 leading into the vacuum chamber 16.

The end of the vessel 12 remote from the mouth opening 18 is domed and has a portion of increased wall thickness, generally indicated by reference numeral 20. A hole 22 extends through the portion of increased wall thickness 20 from the interior of the vessel 12 to the exterior thereof.

The vessel 12 is typically formed as a unitary moulding of a synthetic plastics material such as polycarbonate.

The vessel 12 defines an outwardly open recess 24 in the wall portion of increased thickness 20 adjacent to the hole 22.

Figures 4, 5:
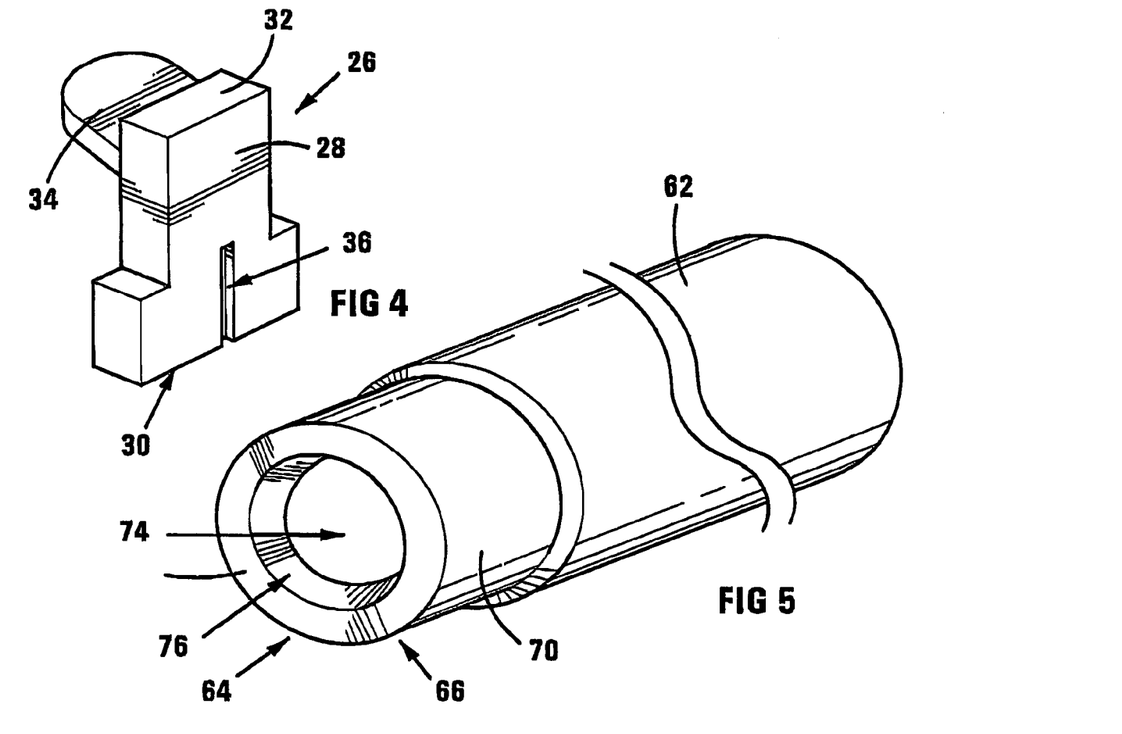
FIG. 4 shows a three-dimensional view of a seal element forming part of the device of FIG. 1.
FIG. 5 shows a three-dimensional view of a pump on which a seal arrangement forming part of apparatus for the treatment of erectile dysfunction in accordance with the invention is mounted.

The valve arrangement 14 includes a support 26 which, as can best be seen in FIGS. 3 and 4, has a generally inverted T-shaped body 28 having an operatively lower end 30 and an operatively upper end 32. The valve arrangement 14 further includes a seal element 34 which protrudes from the body 28. An upwardly extending slot 36 extends from the lower end 30 of the body 28 upwardly therefrom for part of the length of the body. The support 26 is dimensioned such that the body 28 is snugly receivable in the recess 24. In this regard, the provision of the slot 36 facilitates insertion of the body 28 into the recess 24 by permitting the air to escape from the recess 24.

As can best be seen in FIG. 2 of the drawings, the surface 35 of the vessel 22 out of which the operatively outer end of the hole 22 opens, is inclined. As a result of the natural resilience of the material of the body 28 and seal element 34, the seal element is urged into sealing abutment with the surface 35.

In addition, the side 37 of the recess 24 furthest from the hole 22 extends, initially, upwardly from the base of the recess 24, parallel with the hole 22 and then outwardly away from the hole 22.

Hence, the body 28 is displacable, between a rest position, shown in solid lines in FIG. 2 of the drawings, towards which it is biassed, and in which the seal element 34 functions as a flap valve or non-return valve to inhibit the flow of air through the hole 22 into the vacuum chamber 16, and a displaced position, shown in broken lines in FIG. 2 of the drawings, in which the upper portion of the body 28 is displaced in the direction of arrow 38 so that the seal element 34 is displaced clear of the hole 22 permitting the flow of air therethrough. To facilitate displacement of the body 28 from its rest position towards its displaced position, the seal element 34 is connected to the body 28 at a position spaced from the upper end 32 of the body 28. Hence, a portion of the body 28 protrudes above the connection with the seal element 34. The protruding portion of the body 28 can then be gripped by a person's finger or finger nail to displace the body to its displaced position.

The device 10 includes seal means, generally indicated by reference numeral 40 positioned in the vicinity of the mouth opening 18. The seal means 40 is in the form of a constriction ring 42 comprising a body of a resiliently deformable material such as silicone rubber. The constriction ring 42 includes a central opening 44 surrounded by a tubular central portion or collar 46. A circumferentially extending upwardly directed ring-shaped formation or skirt 48 and a flat annular connecting web or recessed portion 50 extend between the collar 46 and the skirt 48. The skirt 48 has an inner surface or wall 52. The outside diameter of the constriction ring 42 is about 58 mm. The diameter of the wall 52 is about 47 mm. This diameter is slightly smaller than the diameter of the vessel 12 so that the constriction ring 42 is sealingly received or engaged on the end of the vessel 12 by friction fit. In different embodiments of the invention, the central opening 44 has a diameter of 13 mm to 24 mm.

Figure 6:
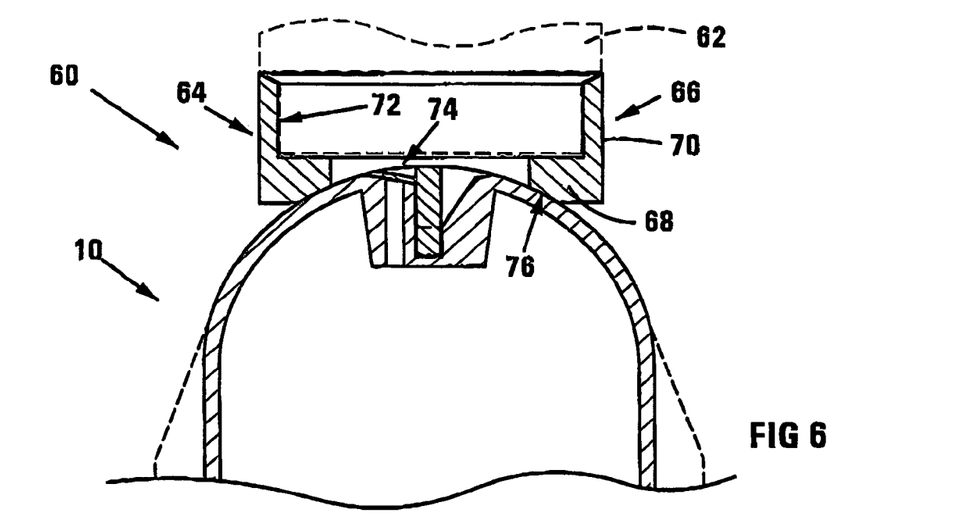
FIG. 6 shows the seat arrangement being held in abutment with the device of FIG. 1 in order to draw a vacuum in the vacuum chamber of the device.

Reference is now made to FIGS. 5 and 6 of the drawings, in which reference numeral 60 refers generally to apparatus in accordance with the invention. The apparatus 60 includes, in addition to a device 10, a vacuum pump 62 and a seal arrangement, generally indicated by reference numeral 64.

The vacuum pump 62 is a conventional electrically operated vacuum pump such as that which is used in the system available under the trademark "POS-T-VAC".

The seal arrangement 64 includes a body 66 which is formed of a resiliently deformable material such as silicone rubber. The body 66 comprises a flange member 68 from which an annular collar 70 protrudes. A radially inner surface 72 of the collar 70 defines a pump engaging seat which is sealingly receivable on a circular cylindrical portion of the vacuum pump 62. A centrally disposed hole 74 extends through the flange member 68. A surface of the member 68 around the hole 74 has an annular concave part spherical recess 76 therein. The recess 76 forms a vessel engaging seat for sealingly engaging the surface of the vessel 12 around the hole 22 as described in more detail here below. Naturally, the pump engaging seat and vessel engaging seat will be configured to suit the pump and vessel with which the seal arrangement is intended to be used.

The invention extends to a seal arrangement as described above.

In use, with the body 66 mounted on the vacuum pump 62, the recess 76 is brought into abutment with the surface of the vessel 12 such that it surrounds the hole 22. In this regard the hole 74 is sufficiently large that precise alignment of the pump 62 with the device 10 is not required.

The flaccid penis of a user (not shown) is drawn into the vessel 12 of the device 10, through the opening 44 of the constriction ring 42 by operating the vacuum pump 62. By operating the vacuum pump 62, air is drawn from the interior of the vessel 12 through the hole 22 past the seal element 34. This reduces the air pressure in the vacuum chamber 16 causing the flaccid penis to be drawn into the vessel 12. Continued use of the pump 62 results in the air pressure in the vacuum chamber 18 being reduced and blood is drawn into the penis to achieve an erection of the penis in the vacuum chamber 16.

The constriction ring 42 seats sealingly around the penis. The vacuum pump 62 causes a pressure drop in the vacuum chamber 16 of about −0.4 bar. This is sufficient to draw the penis into the vessel 12 and to drawn blood into the penis 12 to cause an erection.

The collar 46 is deformed by the drawing of the penis into the opening 44 thereby causing the seal-penis contact area to be increased by the draping of the collar 46 onto the penis, collar-fashion.

When the desired vacuum has been drawn in the vacuum chamber 16, the vacuum pump 62, which is held in position by hand, is simply switched off and removed. The vacuum which has been drawn in the vacuum chamber 16 is maintained by virtue of the closure of the seal element 34.

Once an erection is achieved, the vessel 12 is simply disengaged from the constriction ring 42 which remains in place on the erect penis. In the event that, as a result of the vacuum existing within the vacuum chamber 16, difficulty is encountered in disengaging the vessel 12 from the constriction ring 42, the upper end 32 of the body 28 can be displaced in the direction of arrow 38 thereby unseating the seal element 34 permitting the vacuum in the vacuum chamber 60 to be relieved. The vessel 12 can then be disengaged from the constriction ring 42 relatively easily.

The diameter of the opening 44 is selected so that the blood flow from the erect penis is constricted thereby maintaining the erection.

In the case of penile exercise, the diameter of the opening 44 is selected by a user so that the constriction ring engages sealingly with the penis during the drawing of the vacuum so that an erection is achieved but not so that blood flow from the penis is constricted when the vacuum is relieved. Thus when the vacuum is relieved blood flow from the penis relaxes the erection. Such penile exercises are believed to function as a treatment of erectile dysfunction.

Figure 7:
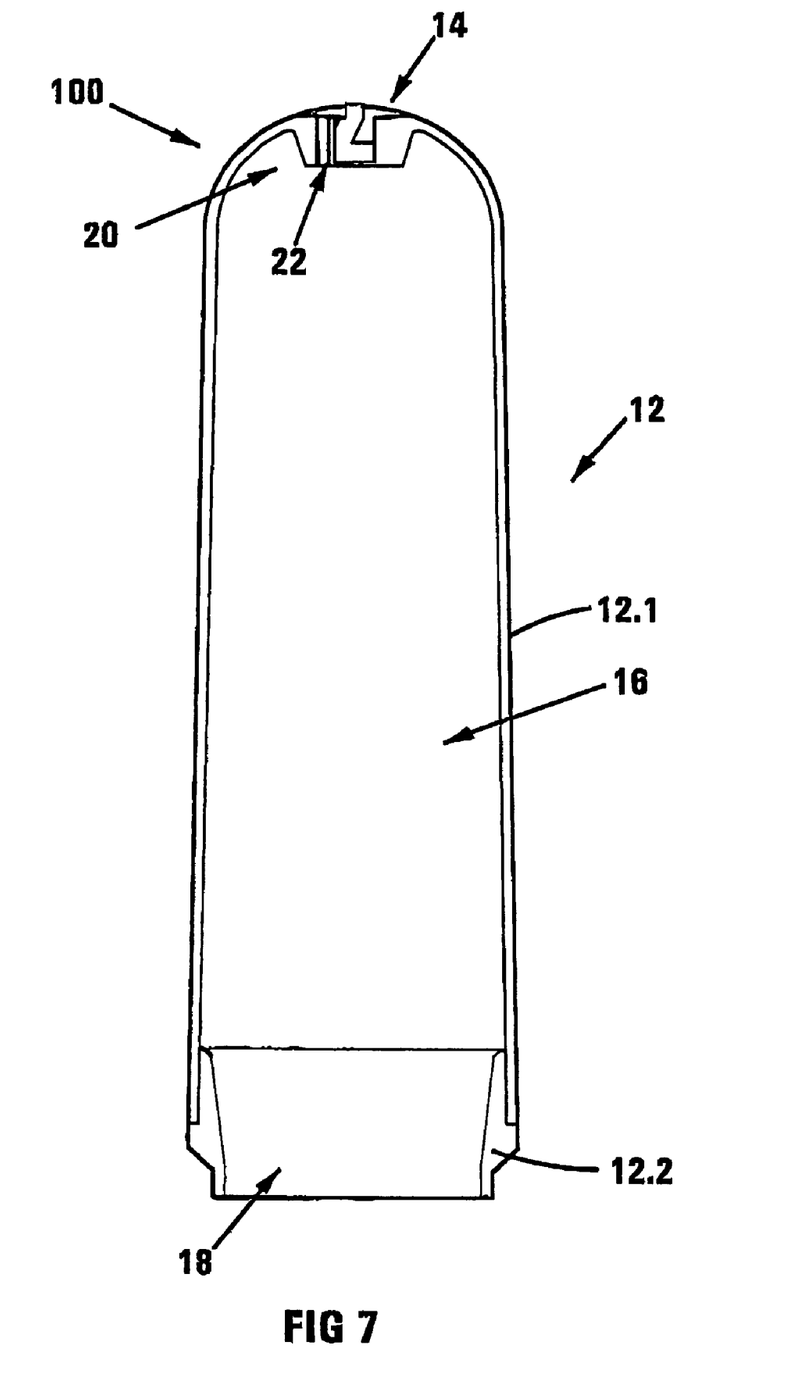
FIG. 7 shows a sectional side view of another device for use in the treatment of erectile dysfunction in accordance with the invention.
Figure 8:
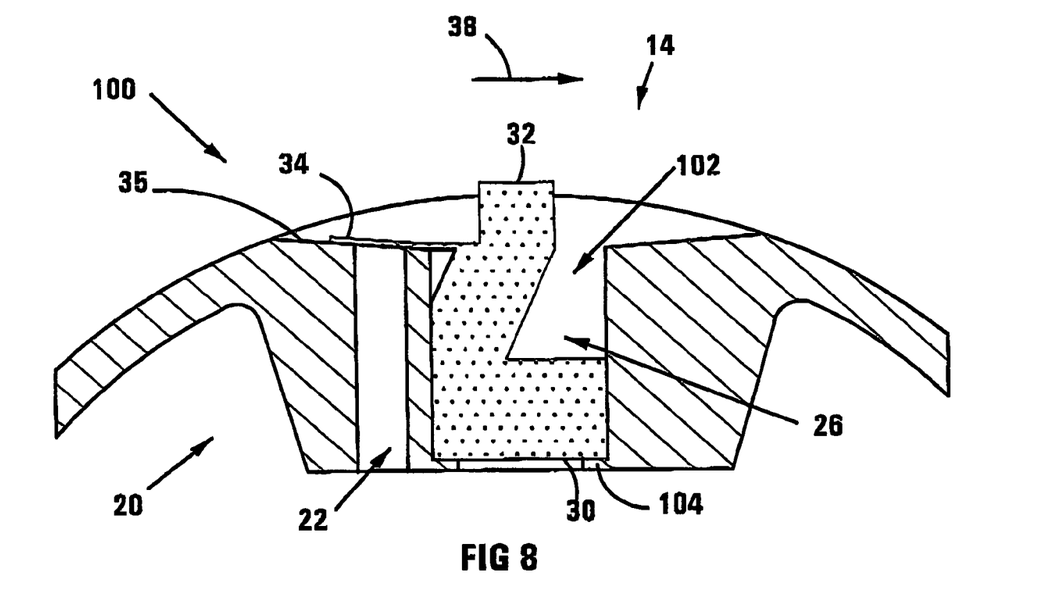
FIG. 8 shows, on an enlarged scale, a sectional view of an end portion of the device of FIG. 7.
Figure 9:
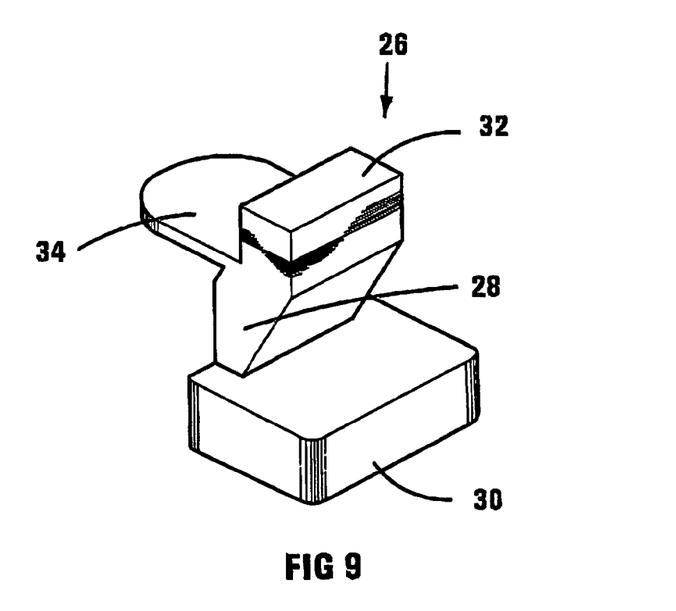
FIG. 9 shows a three-dimensional view of a seal element forming part of the device of FIG. 7.

Reference is now made to FIGS. 7 to 9 of the drawings, in which reference numeral 100 refers generally to another device for use in the treatment of erectile dysfunction in accordance with the invention and, unless otherwise indicated, the same reference numerals used above are used to designate similar parts.

In order to facilitate manufacture, the vessel 12 is formed in two parts 12.1 and 12.2, each of which is formed as a unitary moulding of a synthetic plastics material such as polycarbonate. The parts 12.1 and 12.2 are then secured together, e.g. adhesively. Further, in order to facilitate the moulding of the part 12.1 a centrally disposed hole 102 extends through the wall portion 20 to permit the stabilization of a core positioned within a mould within which the part 12.1 is to be moulded. An annular shoulder 104 is provided at the inner end of the hole 102. In this embodiment of the invention, the support 26 is shaped and dimensioned such that it is sealingly received in the hole 102 to form a gastight seal therein.

The device 100 is used in substantially the identical fashion to the device 10.

It will further be appreciated that, if desired, the valve arrangement 14 could be provided on a device having a manually operable pump such as that described in South African Patent No 99/1676, which is incorporated herein by reference, thereby permitting the device to be used both manually and with a vacuum pump as desired.

Figure 10:
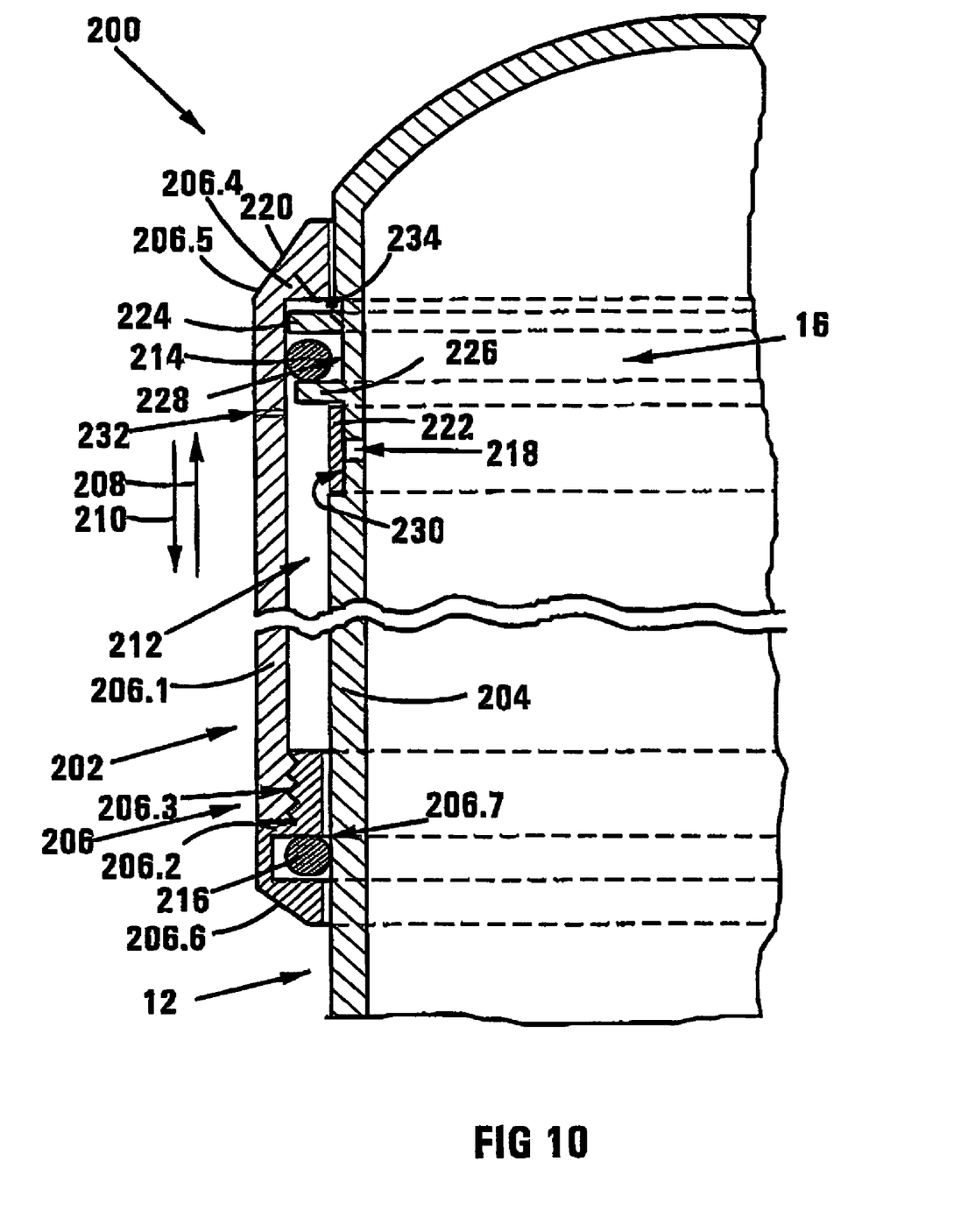
FIG. 10 shows a sectional side view of part of yet another device for use in the treatment of erectile dysfunction in accordance with the invention.

In this regard, reference is now made to FIG. 10 of the drawings, in which reference numeral 200 refers generally to yet another device for use in the treatment of erectile dysfunction in accordance with the invention and, unless otherwise indicated, the same reference numerals used above are used to designate similar parts.

In this embodiment, the device 200 includes supplementary pumping means, generally indicated by reference numeral 202.

The vessel 12 has a generally cylindrical side wall 204. The supplementary pumping means 202 includes a cylindrical pumping member or sleeve 206 which is mounted on and slidingly displaceable relative to the vessel 12 in the directions of the arrows 208, 210. The sleeve 206 and the vessel 12 are configured so that, together, they form an annular secondary or suction chamber 212. Displacement of the pumping member or sleeve 206 in the direction of arrow 210 will increase the volume of the suction chamber 212 and displacement in the direction of arrow 208 will decrease the volume of the suction chamber 212. The supplementary pumping means 202 further includes sealing means in the form of a pair of O-rings 214, 216 and pumping passages 218 in the wall 204 of the vessel 12 which provide a flow path for air to flow from the vacuum chamber 16 to the suction chamber 212. Four pumping passages 218 are provided, arranged in diametrically opposed pairs. The pumping means 202 includes upper exhaust passages, indicated by the dotted lines 220 which allow air in the suction chamber 212 to be discharged to atmosphere when the pumping member or sleeve 206 is moved in the direction of arrow 208. The pumping means 202 further includes one way valve means in the form of a flat rubber band 222 extending around the cylindrical vessel 12 to cover the pumping passages 218.

The sleeve 206 comprises a top part 206.1 and a bottom part 206.2 which are screw threadedly joined by complementary screw threads generally indicated by reference numeral 206.3 with a lower portion of the upper part 206.1 overlapping an upper portion of the lower part 206.2 at the screw threads 206.3. This allows the device 200 to be disassembled. The upper part 206.1 has an upper inwardly directed collar 206.4 with a tapered upper face 206.5. The lower part 206.2 has a complementary tapered lower face 206.6. The lower part 206.2 has a circumferentially extending inwardly directed recess 206.7 and the O-ring 216 is positioned in the recess 206.7. The O-ring 216 is configured so that it sealingly and slidingly abuts the wall 204 of the cylindrical vessel 12 to provide an airtight seal between the vessel 12 and the pumping member or sleeve 206.

A collar 224 projects outwardly from the wall 204 below the inwardly directed collar 206.4 of the sleeve 206. The exhaust passages 220 are formed by spaced recesses in the collar 224. A second outwardly projecting collar 226 is located below the collar 224 and the wall 204 of the vessel 12 between the collars 224 and 226 is recessed. The collar 224 projects slightly further from the wall 204 of the vessel 12 than does the collar 226. This allows the sleeve 206 to slide smoothly over the collar 224 which thus acts as a guide for accurate "centering" of the sleeve 206. The collars 224, 228 define between them an annular cavity 228 and the O-ring 214 is positioned in the cavity 228. The O-ring 214 has a diameter which is selected so that it abuts slidingly and sealingly against the inside face of the sleeve 206. A further recessed portion 230 in the wall 204 of the vessel 12 is provided below the collar 226 and the pumping passages 218 extend through the wall 204 of the vessel 12 in the recessed portion 230. The rubber band 222 is located in the recessed portion 230 and covers the pumping passages 218. A vacuum relief hole 232 may be provided in the top part 206.1 of the sleeve 206 adjacent the upper O-ring 214 to release vacuum when the sleeve 206 is in its lowermost position.

A circumferentially extending rubber stop member 234 is provided above the collar 224 to dampen the sound of the sleeve when it is reciprocated.

The device 200 includes a valve arrangement 14 (not shown).

In use, the device 200 can be used in substantially identical fashion to the device 10, 100. Alternatively, if a vacuum pump 62 is not available, use can be made of the supplementary pumping means 202. In this case, if the sleeve 206 is moved upwardly, i.e. in the direction of arrow 208, the O-ring 214 is displaced upwardly so that it abuts against the collar 224 and is clear of the collar 226. In addition, the volume of the suction chamber 212 is reduced and air in the suction chamber is driven past the O-ring 214 and the collar 226 and out through the exhaust passages 220. When the sleeve 206 is moved in the direction of arrow 210, the O-ring 214 is displaced downwardly and abuts sealingly against the collar 226 thereby forming an airtight seal between the sleeve 206 and the vessel 12. In addition, the volume of the suction chamber 212 is increased so that air is sucked via the pumping passages 218, under and past the rubber band 222, which acts as a one way valve by allowing air flow from the vacuum chamber 16 to the suction chamber 212 but preventing air flow in the opposite direction. On the return stroke of the sleeve 206 air is again exhausted via the exhaust openings 220. The O-ring 214 hence functions as a one way valve. In this way by reciprocating movement of the sleeve 206, air is drawn out of the vacuum chamber 16 thereby, when the mouth is closed, incrementally reducing the pressure in the vacuum chamber 16. It will be appreciated that if desired, the O-ring 216 can function as a one way valve in addition to the O-ring 214.

It will be appreciated that the device 10, 100, 200 can be a lightweight plastics material. This combined with the fact that the pump is not physically connected to the vessel, i.e. is simply held in contact with the vessel by hand, makes the device more compact and more natural then other devices of which the inventor is aware. Further, once the vacuum is drawn, the pump is removed immediately which results in the device 10, 100, 200 providing minimum interference and discomfort in an intimate situation.

The invention claimed is:

1. A device for use in the treatment of erectile dysfunction or for penile exercise which includes:
    an elongate vessel defining a vacuum chamber and having at one end of the vessel a mouth opening leading into the vacuum chamber, the vacuum chamber being shaped and dimensioned to receive a penis; and
    a valve arrangement positioned at or towards the other end of the vessel, the valve arrangement incorporating both a non-return valve to permit air to be extracted from and a vacuum to be drawn in the vacuum chamber, and a selectively operable vacuum relief valve, the valve arrangement including a hole extending through the vessel and a seal element displaceable between a closed position, towards which it is biased, and in which it permits the flow of air from inside the vessel through the hole to outside the vessel and inhibits flow of air from outside the vessel to inside the vessel, and an open position which permits the flow of air through the hole both into and out of the vessel the seal element being in the form of a resilient deformable flap which functions in its closed position as a non-return valve to permit air to be drawn from the vacuum chamber and inhibit the flow of air into the vacuum chamber.

2. A device as claimed in claim 1, in which the seal element is mounted on a support which is mounted on the vessel and at least part of which is displaceable between a rest position towards which it is biased, in which the seal element functions as a non-return valve and a displaced position, in which the seal element is displaced to its open position in which it is clear of the hole to permit air flow therethrough.

3. A device as claimed in claim 2, in which the seal element and the support are formed as a unitary moulding of a synthetic plastics material.

4. A device as claimed in claim 1, which includes seal means positioned in the vicinity of the mouth opening and configured to engage with an outer surface of a human penis inserted into the vacuum chamber.

5. A device as claimed in claim 4, in which the seal means includes a sealing constriction ring which is readily dismountably mounted on the vessel in the vicinity of the mouth opening, the constriction ring including a generally ring-shaped body having a circumferentially extending engagement formation for releasable sealing engagement with the vessel in the vicinity of the mouth opening and a constriction ring opening configured sealingly to abut against the outer surface of a human penis.

6. A device as claimed in claim 5, in which the body of the constriction ring is formed as a unitary moulding of an elastomeric material.

7. A device as claimed in claim 6, in which the elastomeric material is silicon rubber having a hardness of about 50 A Shore.

8. A device as claimed in claim 5, in which the constriction ring opening has a diameter of between 13 and 30 mm.

9. A device as claimed in claim 5, which includes a plurality of interchangeable sealing restrictions rings, each having a constriction ring opening of a different size.

10. A device as claimed in claim 1, which includes supplementary pumping means, at least part of which is mounted for reciprocation relative to the vessel, for pumping air out of the vacuum chamber.

11. A device as claimed in claim 10, in which the supplementary pumping means includes
    a pumping member, mounted on and slidingly displaceable relative to the vessel, the vessel and pumping member being shaped and configured so that the vessel and the pumping member together form a suction chamber and so that sliding displacement of the pumping member and the vessel relative to one another changes the volume of the suction chamber;
    at least one pumping passage extending between the vacuum chamber and the suction chamber;
    at least one exhaust passage leading from the suction chamber;
    first one way valve means which permits fluid flow from the vacuum chamber to the suction chamber via the, or each, pumping passage; and
    second one way valve means which permits fluid to be discharged from the suction chamber via the or each exhaust passage to atmosphere.

12. A device as claimed in claim 11, in which the vessel has an outer surface which is substantially cylindrical for at least part of its length, the pumping member extending around the cylindrical portion of the outer surface of the vessel and being longitudinally slidingly displaceable relative thereto.

13. A device as claimed in claim 12, in which the or each pumping passage is positioned and the pumping member is arranged so that displacement of the pumping member towards the mouth of the vessel increases the volume of the suction member and causes air to flow from the vacuum chamber through the or each pumping passage into the suction chamber and displacement of the pumping member away from the mouth of the vessel decreases the volume of the suction chamber causing air to be discharged from the suction chamber through the or each exhaust passage to atmosphere.

14. Apparatus for use in the treatment or erectile dysfunction or for penile exercise which includes
    an elongate vessel defining a vacuum chamber and having at one end of the vessel a mouth opening leading into the vacuum chamber, the vacuum chamber being shaped and dimensioned to accommodate an erect human penis;
    a non-return valve mounted on the vessel to permit air to be extracted from and a vacuum to be drawn in the vacuum chamber;
    a vacuum pump which is readily disconnectable connectable in flow communication with the vacuum chamber; and
    a seal arrangement to provide a seal between the vessel and the vacuum pump when the pump is being held manually in position to connect the pump and the vacuum chamber in flow communication thereby to permit a vacuum to be drawn in the vacuum chamber.

15. Apparatus as claimed in claim 14, in which the other end of the vessel, i.e. the end remote from the mouth, is domed and the non-return valve is provided at or towards the other end of the vessel.

16. Apparatus as claimed in claim 15, in which the seal arrangement includes a body which defines a pump engaging seat and a vessel engaging seat for engaging sealingly against the pump and the vessel respectively.

17. Apparatus as claimed in claim 16, in which the vessel engaging seat is of a resiliently deformable material shaped and dimensioned to seat sealingly against an outer surface of the vessel around the non-return valve when held in abutment therewith.

18. Apparatus as claimed in claim 17, in which the vessel engaging seat is annular and has a contact surface which is part spherical in order to contact the domed end of the vessel around the valve.

19. Apparatus as claimed in claim 15, in which the valve arrangement includes a hole extending through the vessel and a seal element displaceable between a closed position, towards which it is biased, in which it permits the flow of air from inside the vessel through the hole to outside the vessel and inhibits flow of air from outside the vessel to inside the vessel, and an open position in which it permits the flow of air through the hole both into and out of the vessel.

20. Apparatus as claimed in claim 19, in which the seal element is in the form of a resiliently deformable flap which functions in its closed position as a non-return valve to permit air to be drawn from the vacuum chamber and inhibit the flow of air into the vacuum chamber.

21. Apparatus as claimed in claim 20, in which the seal element is mounted on a support which is mounted on the vessel and at least part of which is displaceable between a rest position, towards which it is biased, and in which the seal element functions as a non-return valve and a displaced position, in which the seal element is displaced to its open position in which it is clear of the hole to permit air flow therethrough.

22. Apparatus as claimed in claim 21, in which the seal element and the support are formed as a unitary moulding of a synthetic elastomeric material.

23. Apparatus as claimed in claim 19, which includes seal means positioned in the vicinity of the mouth opening and configured to engage with an outer surface of a human penis inserted into the vacuum chamber.

24. Apparatus as claimed in claim 23, in which the seal means includes a sealing constriction ring which is readily dismountably mounted on the vessel in the vicinity of the mouth opening, the constriction ring including a generally ring shaped body having a circumferentially extending engagement formation for releasable or sealing engagement with the vessel in the vicinity of the mouth opening and a constriction ring opening configured sealingly to abut against the outer surface of a human penis.

25. Apparatus as claimed in claim 24, in which the body of the constriction ring is formed as a unitary moulding of an elastomeric material.

26. Apparatus as claimed in claim 25, in which the elastomeric material is silicon rubber having a hardness of about 50 A Shore.

27. Apparatus as claimed in claim 24, in which the constriction ring opening has a diameter of between 13 and 30 mm.

28. Apparatus as claimed in claim 24, which includes a plurality of interchangeable sealing constriction rings, each having a constriction ring opening of a different size.

29. Apparatus as claimed in claim 19, which includes supplementary pumping means, at least part of which is mounted for reciprocation relative to the vessel, for pumping air out of the vacuum chamber.

30. Apparatus as claimed in claim 29, in which the supplementary pumping means includes:

a pumping member, mounted on and slidingly displaceable relative to the vessel, the vessel and pumping member being shaped and configured so that the vessel and the pumping member together form a suction chamber and so that sliding displacement of the pumping member and the vessel relative to one another changes the volume of the suction chamber;

at least one pumping passage extending between the vacuum chamber and the suction chamber;

at least one exhaust passage leading from the suction chamber;

first one way valve means which permits fluid flow from the vacuum chamber to the suction chamber via the, or each, pumping passage; and second one way valve means which permits fluid to be discharged from the suction chamber via the or each exhaust passage to atmosphere.

31. Apparatus as claimed in claim 30, in which the vessel has an outer surface which is substantially cylindrical for at least part of its length, the pumping member extending around the cylindrical portion of the outer surface of the vessel and being longitudinally slidingly displaceable relative thereto.

32. Apparatus as claimed in claim 31, in which the or each pumping passage is positioned and the pumping member is arranged so that displacement of the pumping member towards the mouth of the vessel increases the volume of the suction chamber and causes air to flow from the vacuum chamber through the or each pumping passage into the suction chamber and displacement of the pumping member away from the mouth of the vessel decreases the volume of the suction chamber and causes air to be discharged from the suction chamber through the exhaust passage to atmosphere.

* * * * *